United States Patent [19]

Bezwada et al.

[11] Patent Number: 5,019,094
[45] Date of Patent: May 28, 1991

[54] CRYSTALLINE COPOLYMERS OF P-DIOXANONE AND POLY(ALKYLENE OXIDES)

[75] Inventors: Rao S. Bezwada, Whitehouse Station; Shalaby W. Shalaby, Lebanon, both of N.J.

[73] Assignee: Ethicon, Inc., Somerville, N.J.

[21] Appl. No.: 521,212

[22] Filed: May 9, 1990

[51] Int. Cl.$^5$ .............................................. C08G 63/08
[52] U.S. Cl. .................................... 606/230; 528/354; 525/408
[58] Field of Search ........................ 528/354; 525/408; 606/230

[56] References Cited

U.S. PATENT DOCUMENTS

| 3,795,701 | 3/1974 | Jenkins et al. | 528/354 X |
| 4,052,988 | 10/1977 | Doddi et al. | 128/335.5 |
| 4,452,973 | 6/1984 | Casey et al. | 528/354 |
| 4,643,191 | 2/1987 | Bezwada et al. | 528/354 X |
| 4,653,497 | 3/1987 | Bezwada et al. | 528/354 X |
| 4,838,267 | 6/1989 | Jamiolkowski et al. | 528/354 X |
| 4,882,168 | 11/1989 | Casey et al. | 528/354 X |

OTHER PUBLICATIONS

Kimura et al., Polymer, 1989, vol. 30, Jul.
Reed, Ph.D., Dissertation, University of Liverpool (1978), pp. 301–312.

Primary Examiner—Earl Nielsen
Attorney, Agent, or Firm—Matthew S. Goodwin

[57] ABSTRACT

A crystalline copolymer of p-dioxanone and a poly(alkylene oxide), and absorbable surgical filaments and devices derived therefrom.

16 Claims, No Drawings

CRYSTALLINE COPOLYMERS OF P-DIOXANONE AND POLY(ALKYLENE OXIDES)

BACKGROUND OF THE INVENTION

This invention relates to copolymers derived from p-dioxanone, and especially to such crystalline copolymers which can be readily melt spun to prepare fibers suitable for use as absorbable surgical sutures.

U.S. Pat. No. 4,052,988 (Doddi) discloses the preparation of a p-dioxanone homopolymer and its use as an absorbable surgical suture. This synthetic suture exhibits outstanding physical and biological properties which make it a viable candidate to replace natural sutures such as surgical gut and collagen for numerous applications.

One of the significant hurdles to overcome before surgeons readily accept a synthetic suture over natural sutures is the stiffness of synthetics. As an example, a well known synthetic suture, which can be prepared from a glycolide homopolymer or a copolymer of lactide and glycolide, is typically braided or twisted to prepare a multifilament suture so that the suture has the requisite flexibilty and handling characteristics. One of the goals of the polymer chemist attempting to synthesize polymers suitable for use as absorbable surgical sutures is to prepare a monofilament suture which has handling properties and flexibility comparable to such properties of multifilament, braided sutures commonly used in the art without sacrificing physical properties.

Although the p-dioxanone homopolymer described in the Doddi patent goes a long way in reaching the goal toward the preparation of an absorbable monofilament suture with handling properties and flexibilty as good as a braided multifilament, it would be desirable to develop a polymer composition which has even better flexibility relative to a p-dioxanone homopolymer without compromising its physical or biological properties.

SUMMARY OF THE INVENTION

In one aspect, the invention is a crystalline copolymer of p-dioxanone and an amount of a poly(alkylene oxide) effective to lower the modulus of the copolymer relative to the modulus of a p-dioxanone homopolymer.

In another aspect, the invention is an absorbable surgical filament prepared by melt spinning the crystalline copolymer described above.

The crystalline copolymers of this invention can be readily melt spun using conventional techniques to prepare fibers having the combination of physical and biological properties necessary for use as an absorbable monofilament surgical suture. Monofilaments prepared from the crystalline copolymers have a lower Young's Modulus relative to the Young's Modulus of a monofilament prepared from a p-dioxanone homopolymer. A reduction in the Young's Modulus correlates to a more flexible and pliable filament, and therefore the handling characteristics of the suture are enhanced.

In preferred embodiments, the straight tensile strength and knot tensile strength are substantially equivalent to these properties of a monofilament prepared from a p-dioxanone homopolymer.

Lastly, the in vivo absorption profile and the in vitro breaking strength retention (BSR) of sutures prepared from the copolymers of this invention are comparable to the profiles of sutures prepared from a p-dioxanone homopolymer.

The crystalline copolymers are useful for the preparation of absorbable surgical filaments, especially absorbable monofilament surgical sutures, although these copolymers may find use in the preparation of other surgical devices. For example, the copolymers may be used for the preparation of surgical meshes, surgical staples, hemostatic clips, and the like.

DETAILED DESCRIPTION OF THE INVENTION

In a preferred embodiment, the crystalline copolymers of this invention have a molecular weight as reflected in their inherent viscosity and the ability to develop a degree of crystallinity which render the copolymers suitable for extrusion into fibers or films and for injection molding into surgical devices such as staples. Advantageously, the crystallinity of the copolymers is greater than about 10 percent as measured by x-ray diffraction, so that surgical devices prepared from the copolymer can maintain their dimensional integrity at the elevated temperatures one might encounter during storage. Preferably, the inherent viscosity of the crystalline copolymers ranges from about 0.8 to about 5.0, more preferably from about 1.2 to about 3.5 dl/g in a 0.1 g/dl solution of hexafluoroisopropanol (HFIP) at 25° C. A copolymer with an inherent viscosity below about 0.8 dl/g generally lacks sufficient viscosity to provide suitable melt strength for extrusion or molding, and a copolymer with an inherent viscosity above about 5.0 dl/g is generally too viscous for melt processing at the temperatures desired to avoid polymer degradation.

The poly(alkylene oxides) within the scope of this invention can be linear or branched, monofunctional or polyfunctional, and possess hydroxy or amine functionality, provided that the chosen poly(alkylene oxide) is biocompatible and can react with p-dioxanone. Exemplary poly(alkylene oxides) are listed in U.S. Pat. No. 4,452,973, incorporated by reference herein, but this list is by no means all inclusive.

Preferably, the weight average molecular weight of the poly(alkylene oxide) as measured using gel permeation chromatography ranges from about 1000 to about 50,000, more preferably from about 2000 to about 25,000. Generally, poly(alkylene oxides) with a molecular weight below about 1000 fail to lower the modulus of the crystalline copolymers of this invention, and poly(alkylene oxides) with a molecular weight above about 50,000 may compromise the physical properties of the copolymer.

The preferred hydroxy or amine terminated poly(alkylene oxides) are poly(ethylene oxide), which is commonly referred to as polyethylene glycol (PEG), and poly(ethylene oxide-co-propylene oxide). Poly(ethylene oxide-co-propylene oxide) is sold commercially as Pluronic TM block copolymers of ethylene oxide and propylene oxide, Tetronic TM tetra-functional block copolymers of ethylene oxide and propylene oxide, and Jeffamine TM amine terminated poly(alkylene oxides).

The amount of poly(alkylene oxide) in the composition from which the crystalline copolymer is prepared is desirably within the range of about 2 to about 20 weight percent. An amount below about 2 percent generally will not have the effect of reducing the modules of the copolymer to an appreciable degree, and an amount greater than 20 weight percent may compromise the physical properties of the copolymer, to the extent that the copolymer may no longer be suitable for use as an absorbable surgical suture. A preferred range is between about 3 to about 10 weight percent.

The crystalline copolymers of this invention can be either block copolymers or branched copolymers. Diblock copolymers (—AB—) and triblock copolymers (—BAB—), which are derived from monofunctional and difunctional poly(alkylene oxides), respectively, and branched copolymers, which are derived from polyfunctional poly(alkylene oxides), can be characterized as having the following repeating blocks:

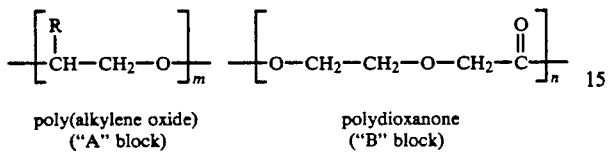

poly(alkylene oxide) ("A" block)   polydioxanone ("B" block)

wherein R is hydrogen or alkyl, and m and n are each a number greater than 1.

The copolymers can be prepared by polymerizing p-dioxanone with the desired type and amount of poly(alkylene oxide) in the presence of an organometallic catalyst at elevated temperatures. The organometallic catalyst is preferably a tin-based catalyst, e.g. stannous octoate, and is present in the monomer mixture at a mole ratio of monomer to catalyst ranging from 15,000 to 40,000/1. The polymerization is typically carried out at a temperature range from 80° to 160° C., preferably 80°–140° C., until the desired molecular weight and viscosity are achieved.

Once the desired crystalline copolymer is prepared, absorbable filaments exhibiting the requisite properties for use as monofilament surgical sutures may be prepared using conventionally accepted methods well known in the art by first melt extruding the copolymer through a spinnerette to prepare fibers, drawing the fibers to create orientation, and then annealing the oriented fibers to enhance dimensional stability. Optimum annealing time and temperature for maximum in vivo BSR and dimensional stability is readily determined by simple experimentation for each fiber composition. Additionally, the sutures prepared from such monfilament fibers can be attached, if desired, to one or more needles.

In preferred embodiments of this invention, absorbable surgical monofilaments prepared from the crystalline copolymers of this invention have a straight tensile strength greater than 50,000 psi, preferably greater than 60,000 psi, and a knot tensile strength greater than 30,000 psi, preferably greater than 40,000 psi. The Young's Modulus for preferred embodiments is typically below 400,000 psi, preferably below 250,000 psi, and more preferably below 100,000.

In the Examples which follow, the in vivo absorption profile and fiber properties shown in the tables, e.g. straight and knot tensile strength, percent elongation and Young's Modulus, are determined using the conventional methods described in U.S. Pat. Nos. 4,653,497 and 4,838,267. In vitro BSR is determined by measuring the percent of original straight tensile strength remaining after the indicated number of days in a phosphate buffer with a pH of 7.27 at 50° C. PDO refers to p-dioxanone.

These Examples are illustrative only and are not intended to limit the scope of the claimed invention, since additional embodiments within the scope of the claimed invention will become readily apparent to those skilled in the art.

EXAMPLE 1

COPOLYMER OF PDO/POLY(ETHYLENE OXIDE-CO-PROPYLENE OXIDE) 96.1/3.9 WT. PERCENT

A flame dried, 250 ml round bottom, single neck flask is charged with 4.18 grams of Pluronic TM F-68 (M.W. 8350) block copolymer of propylene oxide and ethylene oxide. The reaction flask is held under high vacuum at 80° C. for about 18 hours. After cooling to room temperature, the reaction flask is charged with 102.1 gm (1.0 mole, 96.1 wt. percent) of PDO, and 0.101 ml of stannous octoate (0.33 molar solution in toluene). The contents of the reaction flask are held under high vacuum at room temperature for about 16 hours. The flask is fitted with a flame dried mechanical stirrer and an adapter. The reactor is purged with nitrogen three times before being vented with nitrogen. The temperature of the reaction mixture is heated to 110° C. and maintained there for about one hour, lowered to 90° C. and maintained at this temperature for 24 hours, and then lowered to 80° C. and maintained for three days. The copolymer is isolated and dried for 16 hours at 60° C., 16 hours at 70° C., and 32 hours at 80° C. under high vacuum (0.1 mm Hg) to remove any unreacted monomer (about 16%). The copolymer has an inherent viscosity of 3.43 dl/g in hexafluoroisopropenol (HFIP), and a melting point range of 110°–120° C.

EXAMPLE 2

COPOLYMER OF PDO/POLY(ETHYLENE OXIDE-CO-PROPYLENE OXIDE AT 93.6/6.4 WT. PERCENT

The procedure of Example 1 is substantially repeated except that 7 gms of Pluronic TM F-108 (M.W. 14000) block copolymer of propylene oxide and ethylene oxide is reacted with 102.1 gm (1.0 mole) of p-dioxanone, and 0.101 ml of stannous octoate (0.33 molar solution in toluene). The copolymer conversion is 80%, and the copolymer has an inherent viscosity of 3.31 dl/g and a melting point range of 109°–122° C.

Each of the copolymers from Examples 1 and 2 are melt spun, drawn and annealed to prepare oriented, dimensionally stable filaments using conventional extrusion techniques. The physical and biological properties of these filaments are reported in Table 1, which also includes the physical and biological properties of a typical p-dioxanone homopolymer for comparison.

TABLE 1

| PHYSICAL AND BIOLOGICAL PROPERTIES FOR FIBERS OF PDO/POLY(ETHYLENE OXIDE-CO-PROPYLENE OXIDE) COPOLYMERS | | | |
|---|---|---|---|
| Sample No. | Example 1 | Example 2 | Control[1] |
| Initial Weight Composition | Poly(alkylene oxide)/PDO (M.W. 8350) 3.9/96.1 | Poly(alkylene oxide)/PDO (M.W. 14,000) 6.4/93.6 | |
| Inherent Viscosity, dl/g | 3.43 | 3.31 | |
| Melting Point[2] | 110–120° C. | 109–122° C. | |

TABLE 1-continued

PHYSICAL AND BIOLOGICAL PROPERTIES FOR FIBERS OF
PDO/POLY(ETHYLENE OXIDE-CO-PROPYLENE OXIDE) COPOLYMERS

| Sample No. | Example 1 | Example 2 | Control[1] |
|---|---|---|---|
| Fiber Properties | | | |
| (Annealed 6 hrs/80° C./ | | | |
| 5% relaxation) | | | |
| Diameter, mils | 8.09 | 7.90 | — |
| Str. Tensile, Kpsi | 75 | 85 | 76 |
| Knot Tensile, Kpsi | 55 | 55 | 51 |
| Elongation, % | 49 | 47 | 24 |
| Young's Modulus, Kpsi | 167 | 214 | 300 |
| In Vitro BSR at 50° C./7.27 pH | | | |
| Baseline, lbs. | 3.70 | 4.18 | — |
| % BSR, 4 days | 93% | 84% | 82–87% |
| % BSR, 7 days | 78% | 79% | 75–80% |
| In Vivo Absorption | | | |
| % Suture remaining at: | | | |
| 91 days | 74 | 79 | 96 |
| 119 days | 74 | 74 | 83 |
| 154 days | 36 | 27 | — |
| 210 days | 0 | 0 | 0 |

[1]PDS ™ violet monofilament polydioxanone suture.
[2]Determined by hot stage microscopy.

The results from Table 1 illustrate that fibers derived from the copolymers of this invention are more pliable (lower modulus) than fibers derived from a p-dioxanone homopolymer without compromising tensile properties. Significantly, the in-vitro BSR and in-vivo absorption profile are not affected.

EXAMPLE 3

COPOLYMER OF PDO/AMINE-TERMINATED PEG AT 96.7/3.3 WT. PERCENT

The procedure of Example 1 is substantially repeated except that 3.34 g of a monoamine with a PEG backbone containing 30% randomly incorporated propylene oxide (M.W. 2000), sold commercially as Jeffamine ™ M-2070, is reacted with 102.1 gm (1.0 mole) of p-dioxanone, and 0.101 ml of stannous octoate (0.33 molar solution in toluene), and the reaction is conducted 8 hours/110° C. under nitrogen. The copolymer conversion is 85.4%, and the copolymer has an inherent viscosity of 1.69 dl/g, and a melting point range of 107°–109° C.

EXAMPLE 4

COPOLYMER OF PDO/PEG (MONOMETHYL ETHER) At 95.3/4.7 BY WT. PERCENT

The procedure of Example 1 is substantially repeated except that 5 gm of PEG monomethyl ether (M.W. 5000) is reacted with 102.1 gm (1.0 mole) of p-dioxanone, and 0.101 ml of stannous octoate (0.33 molar solution in toluene), and the reaction is conducted about 2 hours at 110° C. and 3 days at 90° C. The copolymer conversion is 83.4%, and the copolymer has an inherent viscosity of 2.06 dl/g and a melting range of 108°–113° C.

Each of the copolymers from Examples 3 and 4 are melt spun, drawn and annealed to prepare oriented, dimensionally stable filaments using conventional extrusion techniques. The physical and biological properties of these filaments are reported in Table II, which also includes the physical and biological properties of a typical p-dioxanone homopolymer for comparison.

TABLE II

PHYSICAL AND BIOLOGICAL PROPERTIES FOR FIBERS OF
COPOLYMERS DERIVED FROM PDO

| Sample No. | Example 3 | Example 4 | Control[1] |
|---|---|---|---|
| Initial weight composition | Poly(alkylene oxide)PDO/ at 3.3/96.7 | Poly(alkylene oxide)/PDO at 4.7/95.3 | — |
| Inherent viscosity, dl/g | 1.69 | 2.06 | — |
| Melting Point[2] | 107°–109° C. | 108–113° C. | — |
| Fiber Properties | Annealed | Annealed | |
| | (6 hrs/80° C./ 5% relax.) | (6 hrs/90° C./ 5% relax.) | |
| Diameter, mils | 7.93 | 7.95 | — |
| Str. Tensile, Kpsi | 83 | 77 | 76 |
| Knot Tensile, Kpsi | 57 | 48 | 51 |
| Elongation, % | 40 | 41 | 24 |
| Young's Modulus, Kpsi | 237 | 223 | 300 |
| In vitro BSR at 50° C./7.27 pH | | | |
| Baseline, lbs. | 4.03 | 4.12 | — |
| % BSR, 4 days | 86 | 82 | 82–87 |
| % BSR, 7 days | 80 | 78 | 75–80 |
| In Vivo Absorption | | | |
| % Suture remaining at: | | | |
| 91 days | 78 | 81 | 96 |
| 119 days | 76 | 77 | 83 |
| 154 days | 56 | 54 | — |

TABLE II-continued
PHYSICAL AND BIOLOGICAL PROPERTIES FOR FIBERS OF COPOLYMERS DERIVED FROM PDO

| Sample No. | Example 3 | Example 4 | Control[1] |
|---|---|---|---|
| 210 days | 0 | 0 | 0 |

[1] PDS ™ Violet monofilament polydioxanone suture.
[2] Determined by hot stage microscopy.

Once again, as observed from the results of Table II, the fibers derived from the claimed copolymers are more pliable than fibers derived from a p-dioxanone homopolymer. The increased pliability of the claimed fibers is achieved without sacrificing tensile properties or biological properties.

What is claimed is:

1. A crystalline copolymer of p-dioxanone and an amount of a poly(alkylene oxide) effective to lower the modulus of the copolymer relative to the modulus of a p-dioxanone homopolymer.

2. The crystalline copolymer of claim 1 wherein the weight average molecular weight of the poly(alkylene oxide) is between about 2000 to about 25,000.

3. The crystalline copolymer of claim 2 wherein the amount of poly(alkylene oxide) is between about 2 to about 20 weight percent.

4. The crystalline copolymer of claim 3 wherein the amount of poly(alkylene oxide) is between about 3 to about 10 weight percent.

5. The crystalline copolymer of claim 4 wherein the poly(alkylene oxide) is poly(ethylene oxide) or a poly(ethylene oxide-co-propylene oxide).

6. The crystalline copolymer of claim 5 wherein the poly(ethylene oxide-co-propylene oxide) is a block copolymer of ethylene oxide and propylene oxide, a tetrafunctional block copolymer of ethylene oxide and propylene oxide, or an amine-terminated poly(alkylene oxide).

7. The crystalline copolymer of claim 6 wherein the crystallinity of the copolymer is greater than about 10 percent as measured by x-ray diffraction.

8. The crystalline copolymer of claim 7 wherein the inherent viscosity of the copolymer is between about 1.2 to about 3.5 dl/g.

9. An absorbable surgical filament prepared by melt spinning the crystalline copolymer of claim 1 or 8.

10. The surgical filament of claim 9 wherein the filament exhibits a straight tensile strength greater than 50,000 psi and a knot tensile strength greater than 30,000 psi.

11. The surgical filament of claim 10 wherein the filament exhibits a straight tensile strength greater than 60,000 psi and a knot tensile strength greater than 40,000 psi.

12. The surgical filament of claim 11 wherein the filament exhibits a Young's Modulus less than 400,000 psi.

13. The surgical filament of claim 12 wherein the filament exhibits a Young's Modulus less than 250,000 psi.

14. The surgical filament of claim 13 wherein the filament exhibits a Young's Modulus less than 100,000 psi.

15. The surgical filament of claim 14 wherein the filament is in the form of a monofilament.

16. The surgical filament of claim 15 wherein the filament is in the form of a suture with or without an attached needle.

* * * * *